Oct. 25, 1932. M. LEENDERS Plant Pat. 38
ROSE
Filed Nov. 3, 1931
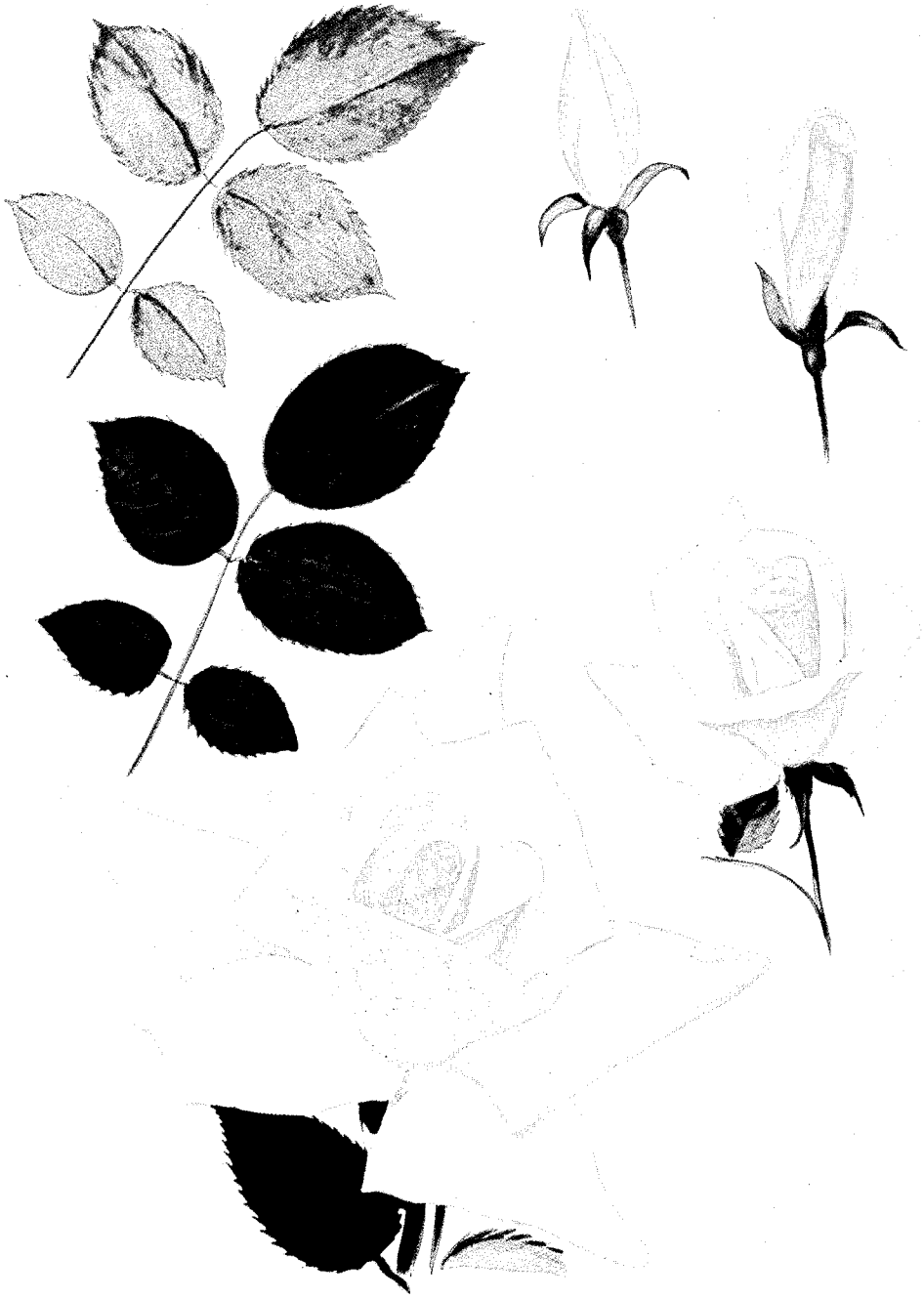
Matthias Leenders
INVENTOR
BY Robb & Robb
ATTORNEYS Patented Oct. 25, 1932

Plant Pat. 38

UNITED STATES PATENT OFFICE

MATTHIAS LEENDERS, OF TEYL, NETHERLANDS, ASSIGNOR TO JACKSON & PERKINS COMPANY, OF NEWARK, NEW YORK, A CORPORATION OF NEW YORK

ROSE

Application filed November 3, 1931. Serial No. 572,853.

The present invention relates to a new variety of rose, the novel characteristics of which reside particularly in the unusual color combination and tout ensemble, and the duration and prolificacy in flowering.

From the standpoint of production, particularly for the cut flower trade, it is a well-known fact that roses generally are not very prolific in blooming characteristics; that is to say, the number of buds or blooms produced per annum or other definite period, is relatively small. Consequently, the return for the care and space required for commercialization is correspondingly restricted. To off-set this lack of prolificacy in otherwise excellent plants, a much greater number must be propagated, which, of course, leads to undue or unprofitable use of time and valuable space.

The present rose, I have found by propagation, possesses the quality of productivity in an unusual or extraordinary degree, and this, together with the fact that the plant is exceedingly robust and healthy, makes the variety especially valuable to producers.

Another characteristic which is a desideratum of considerable importance to the florist, is the long lasting quality, thereby enabling the flowers to withstand handling and shipping unusually well. This long lasting or enduring quality is also valuable to the purchaser as well as to the florist.

The present rose originated from a seedling of Ophelia and Mrs. Aaron Ward, crossed with Souvenir de Claudius Pernet, producing a unique and unusual blending of these three varieties, both in the coloring of the bloom and characteristics of the plant, yet not strictly resembling any one of these.

The accompanying illustrations show in full color, three buds in various stages of maturity, the leaves, and a matured rose.

Referring more specifically to the physical characteristics of the new rose, when the sepals divide, the color of the bud is substantially that of burnt copper or bronze, which lightens as the bud develops. When fully grown, the bud is long and pointed, and as the petals unfurl, there is revealed a tint of chamois or buff lightened with salmon on the inner side of the petals, graduating to gold at the base. However, the reverse side of the petals remains a deep coral, thereby producing a most unusual and unique contrast in rose coloring.

The fully developed flower attains an exceptionally large size as compared with the parents, and is double with a high center. After several days, the outer petals roll outwardly quill-fashion, giving the bloom somewhat the appearance of a cactus dahlia, the deep coral color underneath the petals showing at the tip of the "quills" like a dash of red, thereby adding to the originality of the color combination. The perfume of the flower is delicate but quite pronounced.

The foliage of the plant is characterized by its abundance, the leaves being large and healthy and dark green in color. In the early stages of development, the wood is bronzy-red which gradually turns to dark green with age. The stems are upright and long, generally carrying one bloom each.

The novel color combination of the flower and those characteristics hereinbefore mentioned with relation to the continuity and prolificacy of blooming combine to provide a very desirable and distinctly new commercial product in the rose field.

As a convenient summary, the following description of this new variety is given:—

*Bud.*—Size: Very large. Form: Long pointed. Color: Bronze, copper and buff.

*Bloom.*—Size: Large. Form: Open. High center. Lasting quality: Very good. Fragrance: Moderate. Color: Chamois, salmon and gold inside, deep coral outside. Blooms borne: Singly. On stem: Long. Strong. Petalage: Double. Petal-persistence: Drop off cleanly.

*Foliage.*—Quantity: Abundant. Texture: Leathery. Color: Dark green. Size: Large.

*Barks and twigs.*—Color: Green after reddish brown. Disease-resistance: Resistant. Thorns: Ordinary.

*Growth.*—Vigorous. Habit: Upright.

*Size and aspect of plant.*—That of Mme. Butterfly, 24 to 30″ average height.

*Blooming.*—Quantity: Profuse. Continuous.

*Average hardiness.*—That of hybrid teas.

What I claim as new is:

A new and distinct variety of rose characterized by the bronze color of the flower, the length of the bud, and its prolific habit of growth as shown and described.

In testimony whereof I affix my signature.

MATTHIAS LEENDERS.